United States Patent [19]

Doenges et al.

[11] Patent Number: 5,719,274

[45] Date of Patent: Feb. 17, 1998

[54] PROCESS FOR THE PREPARATION OF LOW MOLECULAR WEIGHT CELLULOSE ETHERS

[75] Inventors: Reinhard Doenges, Bad Soden; Diethart Reichel, Darmstadt, both of Germany

[73] Assignee: Hoechst Aktiengesellschaft, Germany

[21] Appl. No.: 532,414

[22] Filed: Sep. 22, 1995

[30] Foreign Application Priority Data

Sep. 26, 1994 [DE] Germany ............... 44 34 280.2

[51] Int. Cl.⁶ .................. C08B 11/02; C08D 101/28
[52] U.S. Cl. ................. 536/85; 536/90; 536/91; 536/97; 536/98; 536/99; 536/100
[58] Field of Search ................. 536/85, 90, 91, 536/97, 98, 99, 100

[56] References Cited

U.S. PATENT DOCUMENTS 3,108,890 10/1963 Beaver ........................... 106/186
4,420,611 12/1983 Scheve ............................ 536/88

FOREIGN PATENT DOCUMENTS 33 09 465  9/1983  Germany.

*Primary Examiner*—Nathan M. Nutter
*Attorney, Agent, or Firm*—Connolly & Hutz

[57] ABSTRACT

Low molecular weight cellulose ethers which are suitable as a coating material for solid metered units and as an additive in ceramic compositions or cosmetics formulations or as a polymerization auxiliary are obtained by irradiation of a mixture of a higher molecular weight cellulose ether and a base with electrons.

16 Claims, No Drawings

PROCESS FOR THE PREPARATION OF LOW MOLECULAR WEIGHT CELLULOSE ETHERS

FIELD OF THE INVENTION

This invention relates to a process for depolymerizing relatively highmolecular weight cellulose ethers. Another aspect of this invention relates to the resulting low molecular weight cellulose ethers and compositions containing them.

DESCRIPTION OF THE PRIOR ART

The use properties of cellulose ethers are greatly influenced by their molecular weight and the viscosity of their solutions. The molecular weight of cellulose ethers results here from the degree of polymerization and the molecular weight of the polymer base units. High molecular weight cellulose ethers are employed in low concentrations as water-binding agents, thickeners and emulsion stabilizers, for example in medicine, pharmaceuticals, cosmetics and the paper, textile, printing and building materials industry. On the other hand, if the film-formation properties of the cellulose ether are to be utilized, it is necessary to prepare concentrated solutions. This is possible with low molecular weight products, which do not develop a high viscosity in water.

Low molecular weight cellulose ethers can be prepared in principle by two different routes. Either low molecular weight cellulose is used as the starting material and is etherified, or depolymerization down to the desired low molecular weight is carried out during or after preparation of the cellulose ether.

Control of the molecular weight of the cellulose ether by the degree of polymerization of the cellulose employed is the easiest to achieve. However, since commercially available celluloses have a lower limit to their molecular weight, in practice it is as a rule necessary to carry out a depolymerization step, which can be integrated in the production, during preparation of very low molecular weight cellulose ethers.

The molecular weight degradation required for the preparation of low molecular weight cellulose ethers can be carried out using high-energy ionizing radiation, such as electron beams or γ-rays.

Gamma irradiation has several disadvantages compared with electron irradiation. On the one hand, a permanent radiation source requires expensive shielding measures, and the radiation source also emits radiation when not in use. On the other hand, substituents are split off from the cellulose ether in the form of dealkylation and dealkoxylation reactions during the irradiation (F. A. Blouin et al., Textile Research Journal 34, 153–158 (1964)).

DE-A-1,928,045 describes a process for the preparation of water-soluble cellulose ether products of low viscosity by electron irradiation. Higher molecular weight and essentially dry solid cellulose ether products, the moisture content of which is <4% by weight, are employed here as the starting material. The layer of cellulose ether, which is in the form of individual particles, to be irradiated has an essentially uniform depth which approximately corresponds to the penetration depth of the electron beam. This results in essentially all the radiation energy being absorbed and irradiation which is as uniform as possible taking place. The layer of cellulose material to be irradiated is passed through the electron beam at a rate such that the desired radiation dose is achieved. The product treated in this manner is mixed thoroughly after the irradiation, in order to obtain a cellulose ether with properties which are as uniform as possible.

It is furthermore known that the formation of carboxyl groups also occurs during irradiation of solid cellulose material with an electron beam (F. C. Leavitt, J. Polym. Sci. 51 (1961), 349 et seq.; K. Fischer, W. Goldberg, M. Wilke, Lenzinger Berichte 59 (1985), 32 et seq.). After a low radiation dose the pH of an aqueous solution of the irradiated cellulose material already drops significantly due to the acid groups formed. An increase in the radiation dose leads to a further reduction in the pH, which approaches a limit given by the $pK_a$ value and the maximum concentration of acid groups. In time, acid groups impair the storage stability of the cellulose ether and can lead to crosslinkings, which means that the use properties are changed considerably.

Aqueous solutions of cellulose ethers which have been irradiated beforehand in a sufficiently dry state with ionizing radiation, such as γ-radiation or an electron beam, for the purpose of molecular weight degradation show a constantly progressive decrease in viscosity during storage. It is known from U.S. Pat. No. 3,108,890 that such a decrease in viscosity does not occur if the irradiated cellulose ether is dissolved in an aqueous medium and a certain amount of an alkaline compound is then added to this solution, this amount being chosen such that the solution of the cellulose ether has a pH of between 5.5 and 11.5. Alkaline compounds which are employed are alkali metal and alkaline earth metal hydroxides and salts of weak acids, as well as ammonia, amines and quaternary ammonium compounds or complexes.

It is furthermore known from U.S. Pat. No. 2,895,891 that a molecular weight degradation occurs during irradiation of salts of cellulose materials, for example sodium carboxymethylcellulose, with ionizing radiation, regardless of whether the salts of the cellulose materials are irradiated in aqueous solution or in the dry state.

The object of the present invention is to provide a process for the preparation of low molecular weight cellulose ethers such that the low molecular weight cellulose ethers obtained have a high storage stability.

SUMMARY OF THE INVENTION

The invention relates to a process for the preparation of low molecular weight cellulose ethers by irradiation of a higher molecular weight cellulose ether with accelerated electrons, which comprises exposing a mixture of a higher molecular weight cellulose ether and a base to the electron beam.

Higher molecular weight cellulose ethers which have an average molecular weight $\overline{M}_n$ of 50,000 to 500,000 g/mol, depending on the degree of etherification, are used as the starting material. To determine the average molecular weight $\overline{M}_n$ of the cellulose ethers, solutions of the cellulose ethers are measured with an Ubbelohde capillary viscometer and the viscosity-average molecular weight $\overline{M}_n$ is then calculated by the Staudinger method (cf., for example, Krässig, A., "Cellulose: Structure, accessibility and reactivity, Gordon & Breach Science Publishers, Yverdon, Switzerland, 1993, p. 44 et seq.). A solution viscosity in the range from 20 to more than 200,000 mPa.s (measured in accordance with DIN 53015 at 20° C. in a 2% strength by weight aqueous solution in a Höppler falling ball viscometer) corresponds to a viscosity-average molecular weight $\overline{M}_n$ of 50,000 to 500,000 g/mol.

DETAILED DESCRIPTION

All the usual cellulose ethers of correspondingly high molecular weight can be employed in the process according to the invention. They are prepared by known processes by etherification of cellulose in an alkaline medium. Customary etherification reagents for cellulose are, for example, alkyl halides, alkylene oxides or halocarboxylic acids.

As is known in the art, the unetherified cellulose molecule is a β-glycoside, more specifically a chain of hundreds, more typically thousands, of cyclized glucose units linked (at the 1- and 4-positions) by β-glycosidic linkages. Accordingly, the molecular weight of the unetherified cellulose is typically in excess of 100,000 and can be 400,000 or more. Each repeating 1,4-linked glucose unit in the chain has three hydroxyl groups available for etherification, the methylol hydroxyl being the easiest to etherify. Nevertheless up to the full amount of three ether groups per glucose unit can be present in cellulose ethers useful as starting materials for depolymerization according to this invention. Moreover, the ether groups introduced into the cellulose ether can be either nonionic or anionic.

Examples of cellulose ethers useful in this invention include alkylcellulose ethers, for example methylcellulose (MC) or ethylcellulose (EC), hydroxyalkylcellulose ethers, for example hydroxyethylcellulose (HEC) or hydroxypropyl-cellulose (HPC) or mixed ethers thereof, such as alkyl-hydroxyalkylcellulose ethers, for example methylhydroxy-ethylcellulose (MHEC) or methylhydroxypropylcellulose (MHPC), butylhydroxyethylcellulose (BHEC), ethylhydroxy-ethylcellulose (EHEC) or methylhydroxybutylcellulose (MHBC), alkylhydroxyalkylhydroxyalkylcellulose ethers, for example methylhydroxyethylhydroxypropylcellulose (MHEHPC), alkylcarboxyalkylcellulose ethers, for example methylcarboxymethyl-cellulose (MCMC), alkylhydroxyalkylcarboxyalkylcellulose ethers, for examplemethylhydroxyethylcarboxymethylcellulose (MHECMC) or methylhydroxypropylcarboxymethylcellulose (MHPCMC), alkylhydroxyalkylhydroxyalkylcarboxyalkylcellulose ethers, for examplemethylhydroxyethylhydroxypropylcarboxymethylcellulose (MHEHPCMC), or those derivatives of the compounds mentioned which contain sulfoalkyl groups.

Methylcellulose and nonionic or ionic methylcellulose mixed ethers and hydroxyethylcellulose and nonionic or ionic hydroxyethylcellulose mixed ethers are preferably employed in the process according to the invention. Nonionic or ionic methyl- or hydroxyethylcellulose mixed ethers are understood here as meaning cellulose materials which, in addition to the methyl or hydroxyethyl substituents, contain nonionic alkyl and/or hydroxyalkyl substituents and/or ionic carboxy-alkyl or sulfoalkyl substituents having 1 to 4 carbon atoms in the alkyl chain.

Methylcellulose and nonionic methylcellulose mixed ethers, such as methylhydroxyethylcellulose (MHEC), methyl-hydroxypropylcellulose (MHPC) and hydroxyethylcellulose, and nonionic hydroxyethylcellulose mixed ethers, such as hydroxyethylhydroxypropylcellulose (HEHPC), are particularly preferably employed in the process according to the invention.

The cellulose ethers to be employed in the process according to the invention usually have a moisture content of not more than 8% by weight, based on the total weight of the cellulose ether, and a bulk density of 0.2 to 0.7 g/cm³. In the case of bulk goods, the density is stated in the form of the bulk density.

Preferred bases are Arrhenius and/or Brønsted bases, particularly those which are stable—and preferably also soluble—in aqueous media. The $pK_a$ of these preferred bases normally will exceed 8 and will preferably exceed 10. Although bases with $pK_a$ up to 14 in aqueous media are readily obtainable, bases with a buffering action (e.g. bases providing a pH not exceeding 12 or 13 at 0.1 to 10%by weight concentration in water) are preferred, e.g. water-soluble inorganic salts such as the carbonates, bicarbonates, phosphates and/or hydrogen phosphates of highly active metals such as the alkali metals are preferably employed, and the carbonates and/or bicarbonates of the alkali metals are particularly preferred.

The mixture of higher molecular weight cellulose ether and base to be exposed to irradiation with accelerated electrons is usually prepared by first finely grinding and sieving the cellulose ether and the base separately from one another (in the case of cellulose ethers in powder form down to a particle size <200 μm and in the case of cellulose ethers in granule form down to a particle size <500 μm). After the sieving operation, an intimate mixture of the cellulose ether and the basic substance is prepared in a suitable mixing unit or mixing zone, for example a plowshare mixer or an inclined blade mixer.

In another embodiment, the higher molecular weight cellulose ether is sprayed with the aqueous solution of a base and the moist cellulose ether is then subjected to drying by grinding in order to remove the excess water and to establish the abovementioned particle size uniformly.

Thus, it is generally preferred to conduct the irradiation with electrons when the cellulose ether is in a dry, particulate state.

In general, the base content is 0.01 to 4% by weight, based on the cellulose ether. Preferably 0.1 to 2% by weight and particularly preferably 0.1 to 1% by weight of the base is employed, based on the cellulose ether.

Suitable sources of radiation are either continuous or pulsed electron beam accelerators, i.e. a particular radiation dose can be fed to the cellulose ether either continuously with a low intensity or in short intervals with a higher intensity. During the irradiation with electrons, the accelerated electrons penetrate into the irradiated material, and molecules in the irradiated material are thereby excited and ionized (partly with formation of secondary electrons) and bonds in the main chain of the macromolecule are broken to form free radicals, whereby the average molecular weight is reduced.

The energy dose, i.e. the radiation energy transferred per unit weight, is of particular importance for characterizing the process of irradiation with electrons. The unit of the energy dose is the Gray (Gy) [1 Gy=1 J/kg]. The energy dose is usually 5 to 500 kGy.

The penetration depth of high-energy electrons depends on their energy and on the density of the material to be irradiated. The penetration depth s can be calculated empirically from the following formula (formula I)

$$s = 1/\rho(5.1 \cdot E - 2.6) \qquad (I)$$

in which s is the penetration depth in mm, ρ is the density (here: bulk density) of the material to be irradiated in g/cm³ and E is the energy of the beam of accelerated electrons in MeV.

The energy of the beam of accelerated electrons depends on the accelerating voltage. For a material of a given density, the usable penetration depth can thus be adjusted by the choice of accelerating voltage. The bulk density of the higher molecular weight cellulose ethers is in general between 0.2 and 0.7 g/cm³. In principle, it is advantageous to work with accelerating voltages above 1 MV. Preferred accelerating voltages are in the range from 1 to 10 MV, particularly preferably from 5 to 10 MV. To avoid unnecessary heating of the product, it is advisable to carry out the irradiation in several passes each with a fraction of the required total dose if high total energy doses are desired.

At a density (bulk density) of the cellulose ethers to be irradiated of 0.2 to 0.7 g/cm³, the penetration depth s at an accelerating voltage of between 1 and 10 MV is up to about 160 mm.

The energy released to the product, i.e. the energy dose, is not constant over the range of the electrons, which means that the radiation dose absorbed by the product (radiation energy per unit weight) also changes over the range of the electrons.

The optimum penetration depth s(opt) in respect of a radiation dose which is as uniform as possible over the layer thickness of the product under irradiation on one side is as a rule a value of about 2/3.s, at which the radiation energy absorbed on the two product faces is the same, i.e. on the surface of the product facing the radiation source and on that facing away from the radiation source.

A particularly economic utilization of the radiation energy furthermore can be achieved if the product is irradiated from both sides (simultaneously or in succession). In this case, the optimum layer thickness s(opt) is a value of 1.6.s.

The mixture of higher molecular weight cellulose ether and base to be irradiated is usually fed through the beam of accelerated electrons in the form of a layer which is as uniformly deep as possible, for example on a conveyor belt, and at a rate necessary to achieve the desired radiation dose. The layer thickness to be used is determined here in accordance with the abovementioned methods.

The degree of polymerization can be reduced by irradiation of the mixture of higher molecular weight cellulose ether and base with electrons such that the irradiated cellulose ethers have viscosities of down to below 2 mPa.s in a 2% strength by weight aqueous solution (measured in accordance with DIN 53015). The cellulose ethers prepared by the process according to the invention preferably have a solution viscosity of 2 to 50 mPa.s, which corresponds to a viscosity-average molecular weight $\overline{M}_n$ of about 1,000 to 50,000.

The process according to the invention allows the low molecular weight required to be established in a controlled manner without an after treatment being necessary. The cellulose ethers to be employed for the depolymerization can be prepared beforehand without problems by etherification of cellulose of a high degree of polymerization, so that only low washing-out losses and therefore also only a low pollution of the waste water occur.

At the same time, the disadvantages of irradiation with electrons in accordance with the prior art are avoided in that the acid groups which form during irradiation are buffered by irradiation of a mixture of higher molecular weight cellulose ether and base. A low molecular weight cellulose ether of which the aqueous solution has a pH in the range from 6 to 8.5, from which a high storage stability results, is thus obtained.

Surprisingly, it has furthemore been found that both the solubility of the products is significantly improved and the clouding of an aqueous solution of the products decreases after irradiation of the mixture of higher molecular weight cellulose ether and base with electrons (cf. Table 4).

The cellulose ethers prepared by the process according to the invention are therefore suitable for uses where both clear solubility and minimum residue values are essential, such as, for example, cosmetics formulations, solid metered units, additives to ceramic compositions and polymerization auxiliaries. Solid metered units are, for example, tablets, coated tablets and capsules. At the same time, the goods are sterilized by the irradiation with electrons.

The invention is illustrated below by examples.

EXAMPLES

Alkyl substitution is usually described in cellulose ether chemistry by $DS_{alkyl}$. $DS_{alkyl}$ is the average number of substituted OH groups per anhydroglucose unit.

Hydroxyalkyl substitution is usually described by $MS_{hydroxyalkyl}$. $MS_{hydroxyalkyl}$ is the average number of moles of hydroxyalkylation reagent bonded in ether form per mole of anhydroglucose unit.

The viscosity was determined in accordance with DIN 53015 by the method of Höppler in a falling ball viscometer on a 2% strength by weight aqueous solution at 20° C.

Examples 1–4

Irradiation of methylhydroxypropylcellulose ether (MHPC) in the presence of sodium carbonate.

1 kg of a methylhydroxypropylcellulose ($DS_{methyl}$=1.91; $MS_{hydroxypropyl}$=0.19) was sprayed with 100 ml of an aqueous sodium carbonate solution, the concentration of which was chosen such that 0.3 to 0.6% by weight of sodium carbonate, based on the cellulose ether, was employed.

The product was then subjected to drying by grinding.

In Examples 1 to 4, the irradiation with electrons was carried out at a layer thickness of about 6 cm in individual doses of about 10 to 30 kGy and at an accelerating voltage of 10 MV. The viscosities measured and the pH values are listed in Table 1, Example 1 being a comparison example in which the cellulose ether was irradiated under the conditions stated but without the addition of sodium carbonate.

TABLE 1

Irradiation of an MHPC (DS 1.91; MS 0.19) with electrons in the presence of sodium carbonate

| Example | % by weight of Na₂CO₃ | Total dose [Gy] | Viscosity (2% strength by weight) [mPa.s] | pH (2% strength by weight in water) |
|---|---|---|---|---|
| 1 | 0 | 0 | 210 | 5.60 |
|  |  | 20.3 | 39 | 4.34 |
|  |  | 50.3 | 19 | 4.06 |
|  |  | 93.4 | 7.5 | 3.89 |
|  |  | 163.2 | 4.6 | 3.76 |
| 2 | 0.30 | 0 | 170 | 9.91 |
|  |  | 50.3 | 16 | 7.18 |
|  |  | 93.4 | 7.1 | 6.86 |
|  |  | 163.2 | 4.8 | 6.50 |
| 3 | 0.45 | 0 | 170 | 10.41 |
|  |  | 50.3 | 14 | 7.99 |
|  |  | 93.4 | 7.5 | 7.60 |
|  |  | 163.2 | 4.2 | 7.28 |
| 4 | 0.60 | 0 | 150 | 10.46 |
|  |  | 93.4 | 7.1 | 7.57 |
|  |  | 163.2 | 4.2 | 7.30 |

Examples 5 and 6

Studies on methylhydroxypropylcellulose irradiated with electron beams in respect of solubility and clouding properties in aqueous solution.

In Example 6, 1 kg of a methylhydroxypropylcellulose ($DS_{methyl}$ 1.81; $MS_{hydroxypropyl}$ 0.24) was sprayed with 100 ml of an aqueous sodium carbonate solution, the concentration of which was chosen such that 0.15 to 0.6% by weight of sodium carbonate, based on the cellulose ether, was employed.

The product was then subjected to drying by grinding.

The irradiation with electrons was carried out at a layer thickness of about 6 cm in individual doses of about 20 kGy and at an accelerated voltage of 10 MV.

Example 5 is a comparison example in which the cellulose mixed ether was irradiated under the conditions stated but without the addition of sodium carbonate.

After the irradiation with electrons, a 1% strength by weight solution of the irradiated products in water was prepared, the resulting solution was filtered through a filter of pore size 20 μm and the insoluble residue was determined (Table 2).

The clouding properties of the irradiated samples were likewise determined on a 1% strength by weight aqueous solution at a wavelength of 578 nm, the layer thickness investigated being 1 cm.

The extinction values found are listed in Table 2.

TABLE 2

MHPC after irradiation with electrons (radiation dose = 160 kGy) (DS 1.81; MS 0.24)

| Example | % by weight of $Na_2CO_3$ | Residue (%) | Extinction |
|---|---|---|---|
| 5 | 0 | 0.031 | 0.046 |
| 6 | 0.15 | 0.016 | 0.021 |
|   | 0.3 | 0.018 | 0.022 |
|   | 0.45 | 0.019 | 0.017 |
|   | 0.6 | 0.018 | 0.019 |

Example 7

Production of Film-Coated Tablets

Methylhydroxypropylcellulose (MHPC) ($DS_{methyl}$ 8; $MS_{hydroxyalkyl}$=0.24; viscosity=4.8 mPa.s) was employed for the preparation of a coating solution for film-coated tablets.

1 kg of coating solution comprised:

80 g of MHPC 3.5 g of polyethylene oxide 8000

20 g of titanium dioxide 6 g of talc 1 g of iron oxide yellow 889.5 g of water

A film 0.1 mm thick which was smooth and uniform was applied to placebo tablets. The film led to no substantial delay in disintegration of the tablets.

The cellulose ether employed was prepared by mixing 1 kg of MHPC (viscosity=200 mPa.s) with a solution of 6 g of sodium carbonate in 100 g of water and subsequent drying by grinding. Irradiation with electrons at 161 kGy gave a product, a 2% strength by weight aqueous solution of which had a pH of 6.9.

What is claimed is:

1. A process for the depolymerization of a nonionic cellulose ether which comprises:

irradiating a mixture comprising a nonionic cellulose ether starting material and a basic water-soluble inorganic salt, which has a buffer action, with accelerated electrons, the resulting cellulose ether product having a lower molecular weight than the starting material.

2. The process as claimed in claim 1, wherein the cellulose ether starting material has an average molecular weight $\overline{M}_n$ of at least about 50,000 g/mol.

3. The process as claimed in claim 2, wherein the cellulose ether starting material has an average molecular weight $\overline{M}_n$ of 50,000 to 500,000 g/mol.

4. The process as claimed in claim 1, wherein the cellulose ether starting material is a methylcellulose ether or a nonionic methylcellulose mixed ether.

5. The process as claimed in claim 1, wherein the cellulose ether starting material is a hydroxyalkylcellulose ether or a nonionic hydroxyalkylcellulose mixed ether.

6. The process as claimed in claim 1, wherein the said basic water-soluble inorganic salt is an alkali metal carbonate, bicarbonate, phoshphate or hydrogen phosphate.

7. The process as claimed in claim 1, wherein said mixture comprises 0.01 to 4% by weight of the basic water-soluble inorganic salt, based on the weight of the cellulose ether starting material.

8. The process as claimed in claim 7, wherein said mixture contains 0.1 to 2% by weight of the basic water-soluble inorganic salt, on the same basis.

9. The process as claimed in claim 7, wherein said mixture contains 0.1 to 1% by weight of the basic water-soluble inorganic salt, on the same basis.

10. The process as claimed in claim 1, comprising: finely grinding the cellulose ether starting material and the basic water-soluble inorganic salt separately from one another, mixing the resulting ground cellulose ether starting material and ground basic water-soluble inorganic salt together in a mixing unit, and carrying out said irradiating step.

11. The process as claimed in claim 1, wherein the cellulose ether starting material is sprayed with an aqueous solution of the basic water-soluble inorganic salt and the resulting moist cellulose ether starting material is then subjected to drying by grinding.

12. The process as claimed in claim 1, wherein said mixture is arranged into a layer having a thickness of about 1 to 160 mm on a conveying surface and is passed through an electron beam by means of said conveying surface.

13. The process as claimed in claim 1, wherein the bulk density of the cellulose ether starting material is 0.2 to 0.7 g/cm$^3$.

14. The process as claimed in claim 1, wherein the irradiating step is carried out with the aid of a continuous electron beam accelerator.

15. The process as claimed in claim 1, wherein the irradiating step is carried out with an electron beam, and the energy dose of the electron beam is 5 to 500 kGy.

16. An essentially clear solution containing a cellulose ether having an average molecular weight $\overline{M}_n$ of less than 50,000 g/mol prepared by the process of claim 1, said essentially clear solution having an extinction value, when determined on a 1 cm layer of 1% by weight aqueous solution at a wavelength of 578 nm, which is less than about 0.025.

* * * * *